US007671995B2

United States Patent
Lin et al.

(10) Patent No.: US 7,671,995 B2
(45) Date of Patent: Mar. 2, 2010

(54) METHOD FOR IMPROVING SURFACE PLASMON RESONANCE BY USING CONDUCTING METAL OXIDE AS ADHESIVE LAYER

(75) Inventors: Chii-Wann Lin, Taipei (TW); Nan-Fu Chiu, Taipei (TW); Wei-Yi Feng, Taipei (TW); Chia-Chen Chang, Taipei (TW); Kuo-Chuan Ho, Taipei (TW); Chih-Kung Lee, Taipei (TW); Kuang-Chong Wu, Taipei (TW)

(73) Assignee: National Taiwan University, Taipei (TW)

( * ) Notice: Subject to any disclaimer, the term of this patent is extended or adjusted under 35 U.S.C. 154(b) by 186 days.

(21) Appl. No.: 12/048,238

(22) Filed: Mar. 14, 2008

(65) Prior Publication Data

US 2009/0161110 A1    Jun. 25, 2009

(30) Foreign Application Priority Data

Dec. 25, 2007    (TW)    ............................ 96150010 A (51) Int. Cl.
*G01N 21/55*    (2006.01)
(52) U.S. Cl. .................................................... 356/445

(58) Field of Classification Search ....................... None
See application file for complete search history.

(56) References Cited

U.S. PATENT DOCUMENTS

2007/0109541 A1*  5/2007  Imato et al. ................. 356/445

\* cited by examiner

*Primary Examiner*—Gregory J Toatley, Jr.
*Assistant Examiner*—Amanda H Merlino
(74) *Attorney, Agent, or Firm*—Schmeiser, Olsen & Watts (57) ABSTRACT

Surface plasmon resonance (SPR) sensing technique which provides high specificity and accuracy has been an important method for molecular sensing technology. In the past, in order to affix 45 nm gold film onto glass or silicon substrate, several nanometers of chromium (Cr) or titanium (Ti) has been used as adhesive layer for the attachment of Au film. However, the existence of Cr or Ti thin film deteriorates the performance of SPR sensor due to their characteristic optical absorption. Our experimental results have confirmed the uses of conducting metal oxide, specifically, ITO and Zinc Oxide (ZnO) can be used to replace Cr or Ti for better performance in terms of SPR resonant properties (resonant angle and HMBW) and sensitivity enhancement for 3 to 15 times than traditional ones. It would contribute significantly to the SPR applications in both biosensors and gas sensors.

15 Claims, 7 Drawing Sheets

| Concentration gradient displacement | ZnO | ITO | Cr |
|---|---|---|---|
| H2O → 1.25% Alcohol solution | 19.165 | 5.315 | 3.77. |
| 1.25% → 2.5% Alcohol solution | 12.326 | 5.129 | 4.140 |
| 2.5% → 5% Alcohol solution | 18.722 | 11.839 | 10.227 |

METHOD FOR IMPROVING SURFACE PLASMON RESONANCE BY USING CONDUCTING METAL OXIDE AS ADHESIVE LAYER

FIELD OF THE INVENTION

The present invention relates to a method for biochemical tests and gas detections, and more particularly to a method that uses surface plasmon resonance (SPR) for the detection.

BACKGROUND OF THE INVENTION

Biochip becomes increasingly popular in academic, government and private organizations in different countries. For DNA chips, technologies related to DNA binding analysis, sequence detection, quantitative analysis, capillary electrophoresis separation detection, nucleic acid amplification and parallel gene expression analysis become well developed. In the meantime, a series of other analytic methods such as cell separation, cell immunity analysis, and applications integrated with combinatorial chemistry are derived, and the research and development of new medicines to provide a high throughput screening. In addition, material technologies are well developed, and biochips are not only made of silicon, but also made of plastic films and elastomers as well. Up to now, the research and development of biochips emphasizes on the applications of DNA chips and the testing requirements of DNA to develop a series of technologies and products, such as quick DNA inspection analysis technology, DNA cloning and segmentation analysis technology, and integrated DNA analysis system, etc.

Biosensor is the most unique part of a biochip that integrates a biological device as a sensing structure. The biosensor is connected to a transducer to achieve the function of detecting a biological reaction. In the development of related chips, the detection method preferably adopts an optical method to provide a higher sensitivity. Although the fluorescent method is used extensively, yet the surface plasmon resonance (SPR) method can provide an instant measure since SPR does not require pre-labeling, and thus SPR has become an important research tool. A biosensor that uses the optical principle of the surface plasmon resonance (SPR) for a transducer is called a surface plasmon resonance sensor (SPRS). If a dielectric material exists in the testing environment, and the assembly, concentration or composition may vary and cause a change of refractive coefficient, then the kinetic energy of the penetrating light will be reflected onto the change of the SPR resonant angle. The surface plasmon resonance (SPR) will occur at the intersection of a metal and an insulating dielectric material, and the penetrating depth of the electric field perpendicular to the interface and the transversal propagation length shows an exponential attenuation by the excitation of a coupler and a polarized electromagnetic wave (TM-wave). If each sensing area of a chip goes through different activating processes and fixes with different antigens (or antibodies), the sensing area of the chip is combined with its corresponding antigen (or antibody). A successfully bonded analyzing matter will affect the change of intensity of a reflected light, and a matter exceeding the range of the surface plasma wave will not affect the measuring result. Therefore, measurements obtained by the surface plasmon resonance (SPR) method has a high discrimination level.

The invention focuses on the research and development of the applications on optical protein biomolecule examinations and sensing components of a gas SPR chip. With the content of the invention, the accuracy and sensitivity of the SPR sensor are improved effectively. In the researches of proteomes, large-scale studies are focused on protein molecules such as receptors and hormones, in hope of fully understanding the important functions of disease mechanisms, cell operation mechanisms and cell network messages. With such researches, a new medicine can be developed, and particularly the results of the researches have positive effects on medicines having reactions with proteins in cells. The bottlenecks of these researches reside on the huge consumption of manpower and the insufficient sensitivity of detection methods. In the development of gas sensor chips, the detected gas usually comes with a small concentration, and thus it is a primary goal to develop a gas sensor with high sensitivity and accuracy. Regardless of the application for protein biomolecules or gas sensor chips, the surface plasmon resonance sensor (SPRS) detection system of the invention can provide a better application.

SUMMARY OF THE INVENTION

In view of the foregoing shortcomings of the prior art, the inventor of the present invention based on years of experience in the related field to conduct extensive researches and experiments, and finally invented a method Surface plasmon resonance (SPR) is a popular optical method for measuring surface and interface characteristics, which was discovered by physical scientists and applied for the study on the characteristics of metals and dielectric thin films, and a SPR sensor shows an instant and high-sensitivity interactive measurement of biomolecules, and thus is used extensively in the researches of biochemistry. Surface plasmon excitation is produced at a metal or semiconductor interface by light energy, electric energy, mechanical energy and chemical energy. The plasmon excitation effect can be used for measuring a change of reflection intensity, when an incident angle or a wavelength of the light is changed. Regardless of adjusting the angle or wavelength of an incident light, the required thickness and evenness of the metal plated film should meet the standard of 1 nm.

In traditional SPR sensor chips, a gold film of 50 nm thick is fixed onto a glass substrate, and thus a highly active metal including chromium (Cr) or titanium (Ti) of several nanometers used as a chip adhesive layer is developed to increase the adhesive force between the gold film and the glass, but when the thickness of this type of opaque material is up to 5 nm, the incident light will be reflected completely. Although only 1-2 nm of chromium (Cr) or titanium (Ti) was usually plated, such arrangement is obviously not good for the optical property, and has the disadvantage of lowering the sensitivity and reliability of the SPR sensor chip.

Biochips used for analyzing the immunity of biomolecules or sensor chips used for detecting the concentration of a gas should take the size (in a micro scale or even a nano scale) of the sensing object into consideration, and thus the sensitivity of a system is a key index for the application and development of excellent sensors with high competitiveness and reliability is the key. In view of the opaqueness of the intermediate layer made of chromium or titanium metal and used in the manufacturing process of a traditional SPR biochip, the sensor chip greatly lowers the sensitivity and reliability of the sensor chip, even though the adhesive force between the nano gold thin film and the chip header. On the other hand, the sensitivity is lowered greatly, and thus the inventor's research team aims at the aforementioned problem to provide an electron transfer mechanism that adopts specially processed indium tin oxide and zinc oxide thin film between the gold film layers to replace the traditional adhesive layer made of chromium. The invention further improve the SPR curve by using indium tin oxide and zinc oxide thin films to progress the light transmission rate and provide a stable adhesive force in addition, so as to enhance the sensitivity and detection efficiency of the sensors.

The conducting metal oxide nano thin film replaces the traditional high-activity metal thin film adhesive layer, not only solving the adverse infection of the opaque chromium or titanium thin film on the sensitivity of detecting a surface by a SPR chip, but also exciting the activating zinc oxide thin film by the electron transfer mechanism to emit lights as well as synchronously strengthening the surface plasmon resonance (SPR). By applying the conducting metal oxide nano thin film to the biomedical sensing system, and detecting the combining condition of specific biomolecules or gas molecules in the microchannels on the surface of the biomedical chip in accordance with the detection principle of SPR, we can obtain a more sensitive, reliable and practical gas and biomolecule detector that can be more applicable for future developments of multi-channel high throughput detection and high sensitivity portable instruments. The present invention concurrently achieves the effects of high sensitivity and high throughput.

The structure of the invention is not limited to a single-layer film structure only, but the structure can be formed by stacking at least one layer of intermediate layer and a metal layer, such as a three-layer structure having a first metal layer, a first intermediate layer and a substrate layer, or a five-layer structure having a first metal layer, a first intermediate layer, a second metal layer, a second intermediate layer and a substrate, and a multi-layer structure without any limitation on the number of layers, and the structure can have one to twenty metal/intermediate layers, and the metal layer/intermediate layers can be interlaced in different sequences, such as a structure sequentially having the first metal layer, second metal layer, first intermediate layer, second intermediate layer and substrate layer. Further, the metal layer can be made of gold, silver, copper, platinum and palladium or an alloy of the above metals and a wrapping structure. The intermediate layer can be made of zinc oxide, indium tin oxide, carbon nanotube, tin dioxide, titanium dioxide, tungsten oxide or any transparent metal oxide with a good conductivity. The substrate layer can be made of glass, quartz, polymer or any transparent high dielectric thin film.

Figure 9:
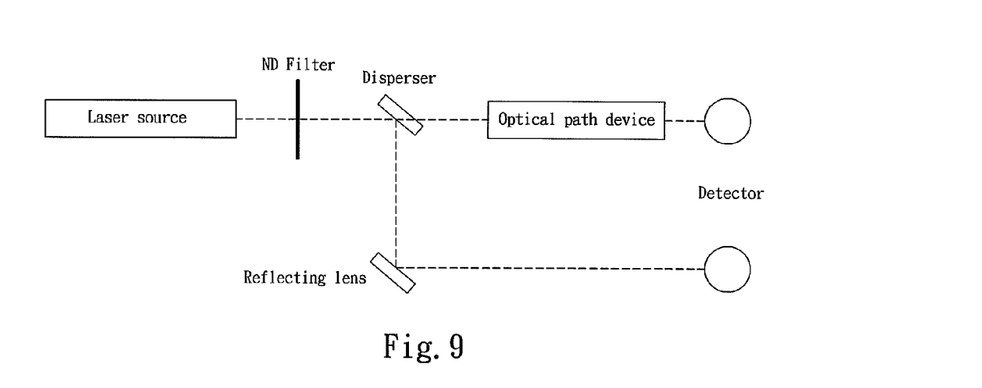
FIG. 9 shows an intensity detecting SPR system in accordance with a preferred embodiment of the invention.
Figure 10:
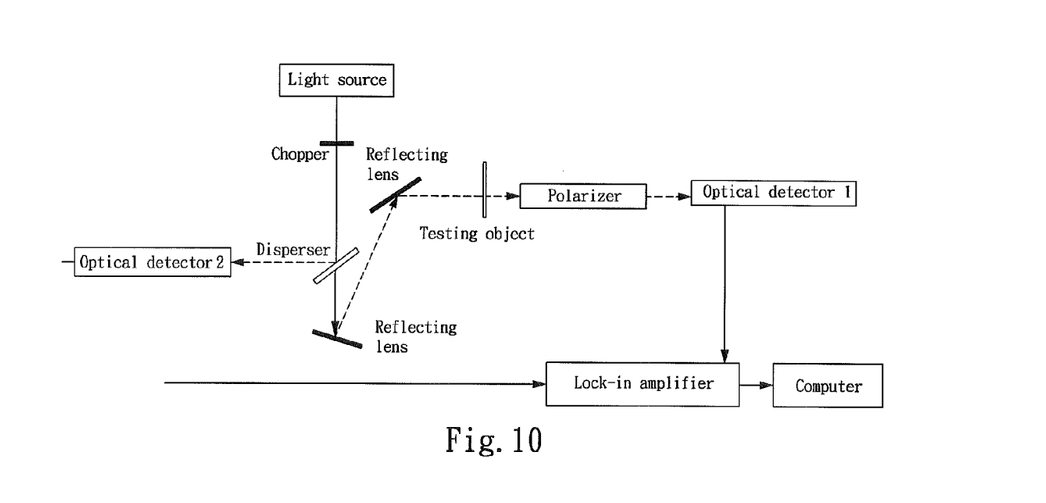
FIG. 10 shows a phase detecting SPR system in accordance with a preferred embodiment of the invention.

The measuring method of the invention is not limited to particular wavelength, intensity or incident angle, wherein the intensity detecting SPR measuring system as shown in FIG. 9 obtains the control intensity variable or the phase detecting SPR measuring system as shown in FIG. 10 controls the incident angle variable, or control the incident light wavelength, and thus the wavelength and intensity of the adopted light source are not specified particularly, and the wavelength ranges from visible light to near infrared light (400 nm to 1700 nm), and dispersion and modulation can be performed, wherein a laser effect with a wavelength of 833 is preferred, an angle of incident light can be 30 to 80 degrees, and preferably 40 to 60 degrees.

The measuring objects of the invention include but not limited to gaseous or liquid biomolecules and chemical compositions, and the biomolecules can be proteins, amino acids, saccharides, lipids, vitamins, minerals, antigens, antibodies, oligos, nucleic acid, oligonucleotides, and the chemical composition can be ethers, alkanes, alcohols, amines, ketones, esters, phenols, liquid inorganic oxides or gas molecules.

DESCRIPTION OF THE PREFERRED EMBODIMENT

The above and other objects, features and advantages of the present invention will become apparent from the following detailed description taken with the accompanying drawing.

Principle of Measuring Surface Plasma Wave and Evanescent Wave

Metal is a conductor filled with free electrons inside. If these electrons are excited by an appropriate variable electric field to produce surface plasmon oscillations and propagated in a waveform along a surface (which is an interface of a metal and a certain dielectric material), and that is a surface plasma wave (SPW or SEW). This phenomenon was discovered by R. W. Wood in the 20$^{th}$ Century during his research on diffractions of a metal surface.

Figure 1:
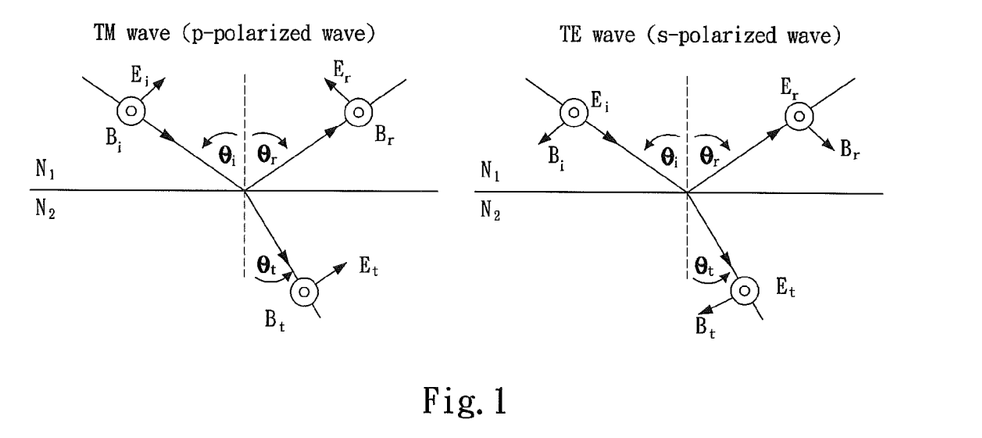
FIG. 1 shows the distribution of electric fields, magnetic fields and light traveling directions of a TM wave and a TE wave.

The aforementioned variable electric field must include a p-polarized light having TM waves, and the vibration direction of its electric field is parallel to the incident plane, and the light is incident into a prism (or a coupler) with an angle greater than the critical angle. In the meantime, a total reflection occurs, and not all of the energies are reflected, since an evanescent field exists in a direction perpendicular to the interface, and the intensity is attenuated exponentially. The evanescent field causes surface polarization, such that if the incident angle of a light wave is equal to the resonant angle of a surface plasma wave, the surface polarization will be resonated with a change of electric field of the incident light and propagated on the interface by a change of surface charge density, and thus the electric field distributed on the surface is the strongest. This phenomenon is called surface plasmon resonance (SPR). In the meantime, the reflected light intensity will drop suddenly, and such phenomenon is called attenuation total reflection (ATR). FIG. 1 shows the electric field, the magnetic field, and the distribution of light traveling directions of the TM wave and TE wave.

SEW is also an evanescent wave, and the maximum electric field occurs at the interface and the intensity of the electric field decreases exponentially with the distance away from the interface. The electric field of the surface plasma wave shows an asymmetric distribution, and the electric field in the metal layer is attenuated faster, and the electric field in the dielectric layer is attenuated slower, and such characteristic makes the change of optical characteristics of the dielectric layer proximate to the surface plasma wave very sensitive. In addition, the surface plasma wave may disappear in the form of light radiation, which is affected by metal thickness and surface roughness, or the surface plasma wave may be changed into heat absorbed into the material.

Matching Conditions of Surface Plasmon Resonance

To cope with the Maxwell's equation and boundary condition, it is necessary to have a coupling relation between the transverse wave vector (kx) and the SPR wave vector (ksp) of the incident light for exciting an external electric field to activate a SPR phenomenon. The dielectric constant between the incident angle and the interface must satisfy the matching condition as listed below to achieve the foregoing objective:

$$\text{Coupling condition: } k_x = \frac{\omega}{c}\sqrt{\varepsilon_p}\ \sin\theta\ \text{matching}\ k_{sp}$$

$$\frac{\omega}{c}\sqrt{\frac{\varepsilon_m(\omega)\varepsilon_s(\omega)}{\varepsilon_m(\omega)+\varepsilon_s(\omega)}}\ \text{(dispersion relation)}$$

The aforementioned coupling phenomenon cannot be achieved by directly projecting light on a metal film surface, but the vector of the wave propagated along the interface must be increased by using an appropriate optical coupler for the activation to produce the coupling. In general, a coupled incident light is guided by a prism, a grating and a light guide, wherein the prism coupling method is adopted extensively in the prior art due to its simple components and easy installation.

Figure 2:
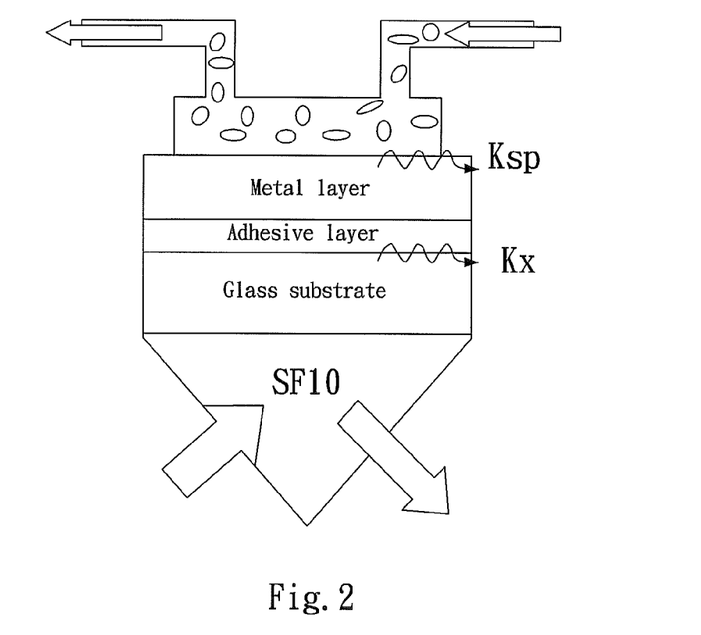
FIG. 2 shows the structure of a SPR detection chip.

Traditionally, chromium is used for an adhesive layer of a SPR sensor chip. In the past, a piece of glass was plated with 1 nm-2 nm chromium to serve as an adhesive layer for effectively attaching a 45 nm gold film onto a glass substrate of a SPR sensor chip to form an adhesive force among gold molecules, and fix the gold film onto the glass substrate for practical applications as shown in FIG. 2.

Figure 3:
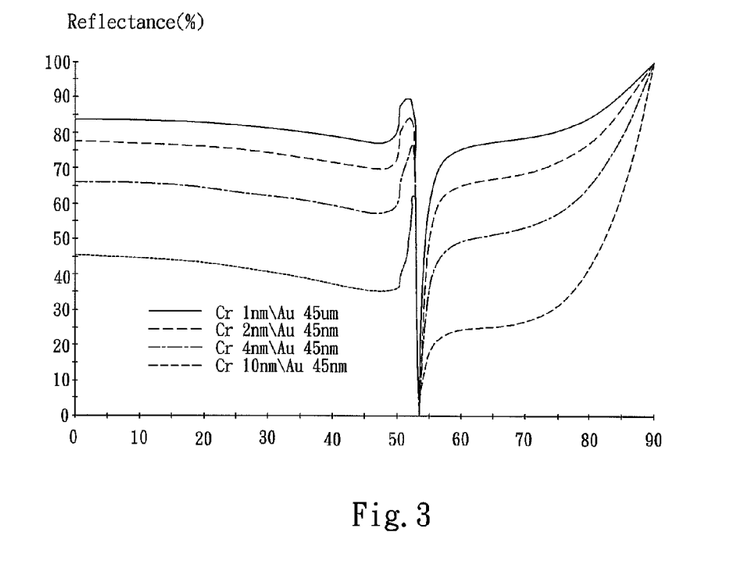
FIG. 3 shows the relation of a reflection intensity and a resonant angle of chromium thin films of different thicknesses.
Figure 4:
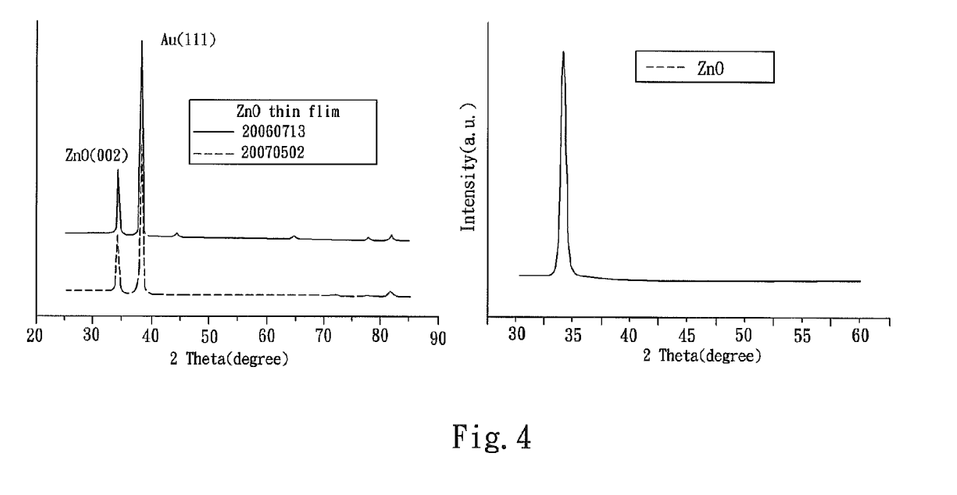
FIG. 4 shows a spectrum of SPR chip using ZnO as an intermediate layer thin film at a X-ray diffractometer.
Figure 5:
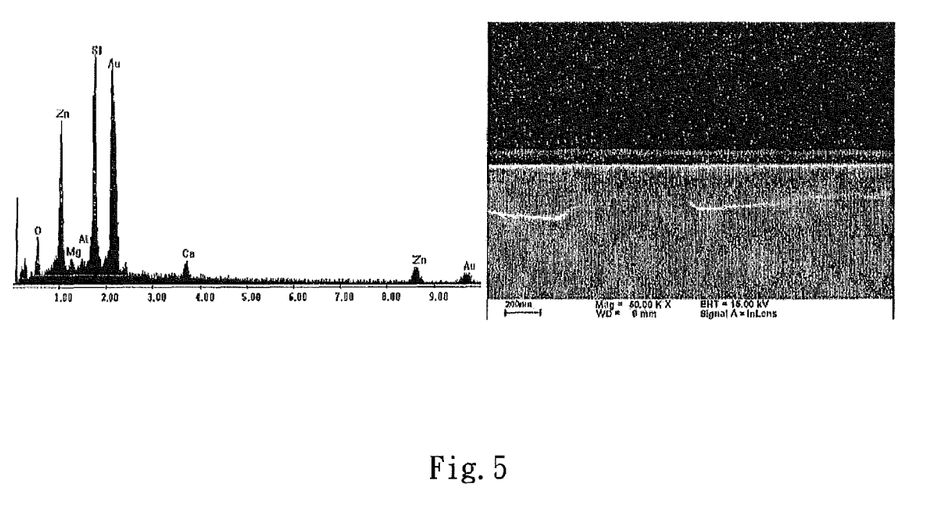
FIG. 5 shows a spectrum of energy diffractometer SPR chip having a 50 nm intermediate layer thin film made of ZnO and a cross-sectional view of SEM.

Since the chromium thin film is opaque, the chromium thin film lowers the SPR sensitivity as shown in FIG. 3. In the invention, a specially processed zinc oxide (ZnO) nano thin film is used to replace the traditional chromium thin film, and enhance the SPR resonant properties and the sensitivity for better biochemical detections and gas sensing applications.

Fabrication Process Technology of Zinc Oxide Sensor Chip and Chip Fabrication Process Nano thin film zinc oxide (ZnO) and indium tin oxide (ITO) processes are used for the deposition of thin films. The power for spluttering and forming ZnO on a RF splutter is set to 150 W, the cavity temperature to 150 degrees, the cavity pressure to 4 m Torr, the concentration of $O_2$ to 30% and Ar to 40%, the deposition time on glass to 30 min, and the film thickness to 50 nm. The power for spluttering and forming ITO on a RF sputter is set to 150 W, the cavity temperature to 100 degrees, the cavity pressure to 10 m Torr, the concentration of $O_2$ to 5%, and Ar to 20%, and the deposition time on glass to 5 min, and the film thickness to 210 nm.

Strengthening Surface Plasmon Resonance (SPR) Mechanism

Figure 6:
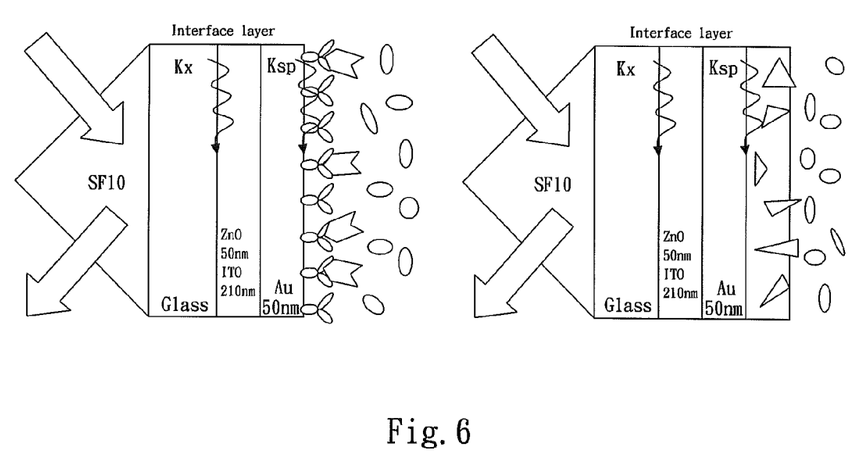
FIG. 6 shows the structure of a SPR detection chip, wherein the left side of the figure shows the structure of a biosensor, and the right side shows the structure of a gas sensor.
Figure 7:
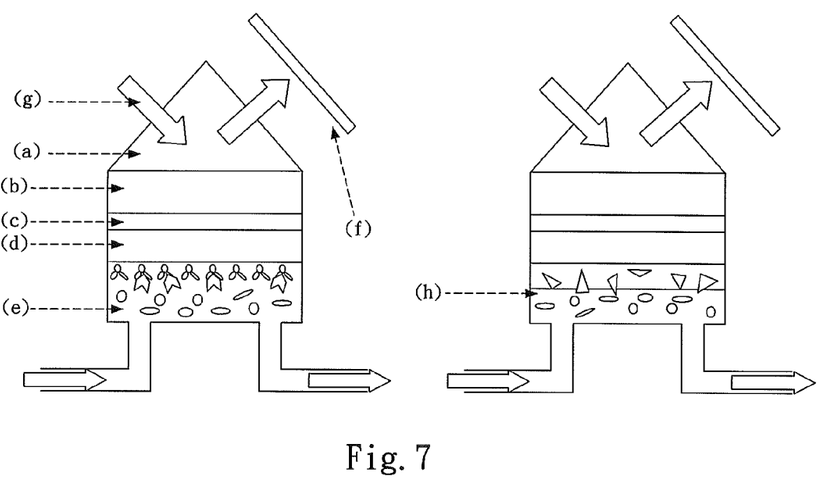
FIG. 7 shows the structure of a SPR detection chip, wherein (a) shows a prism; (b) shows a transparent substrate; (c) shows a second metal layer with appropriate thickness; (d) shows a metal thin film with appropriate thickness, (e) shows a cavity space for sensing identified molecules and testing molecules; (f) shows a detector; (g) shows an incident light source with an appropriate wavelength; (h) shows a cavity space for sensing a gas sensing layer and testing gas molecules.
Figure 8:
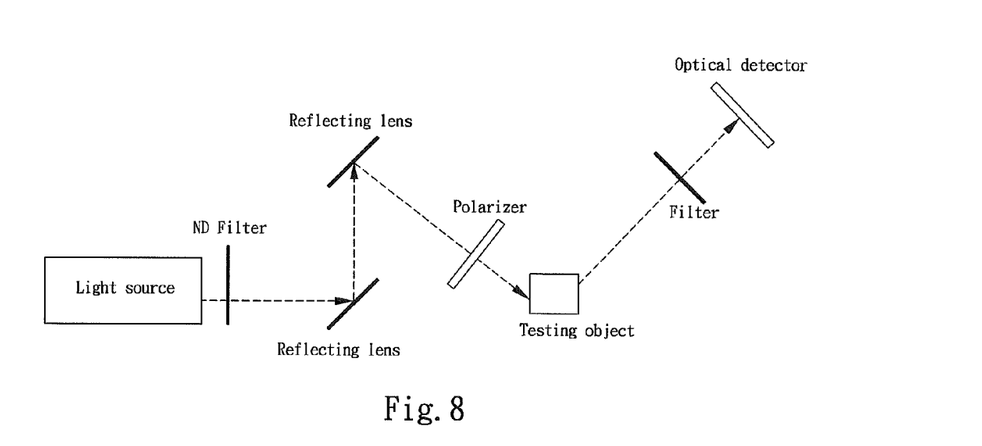
FIG. 8 shows a light intensity measuring system having corresponding propagation length in accordance with a preferred embodiment of the invention.

The structure of a SPR sensor chip is shown in FIG. 6, and a layer of conducting metal oxide is spluttered onto a glass substrate to serve as a chip adhesive layer, and then a gold nano thin film is plated, and finally a biological identified molecule such as an antibody is fixed onto the gold film layer, and polarized light is incident to activate the transverse wave vector (Kx) of the surface plasma wave and produce a coupling with the surface plasma wave SPR wave vector (Ksp) to produce the SPR in order to detect the combination condition of the surface molecules.

Figure 11:
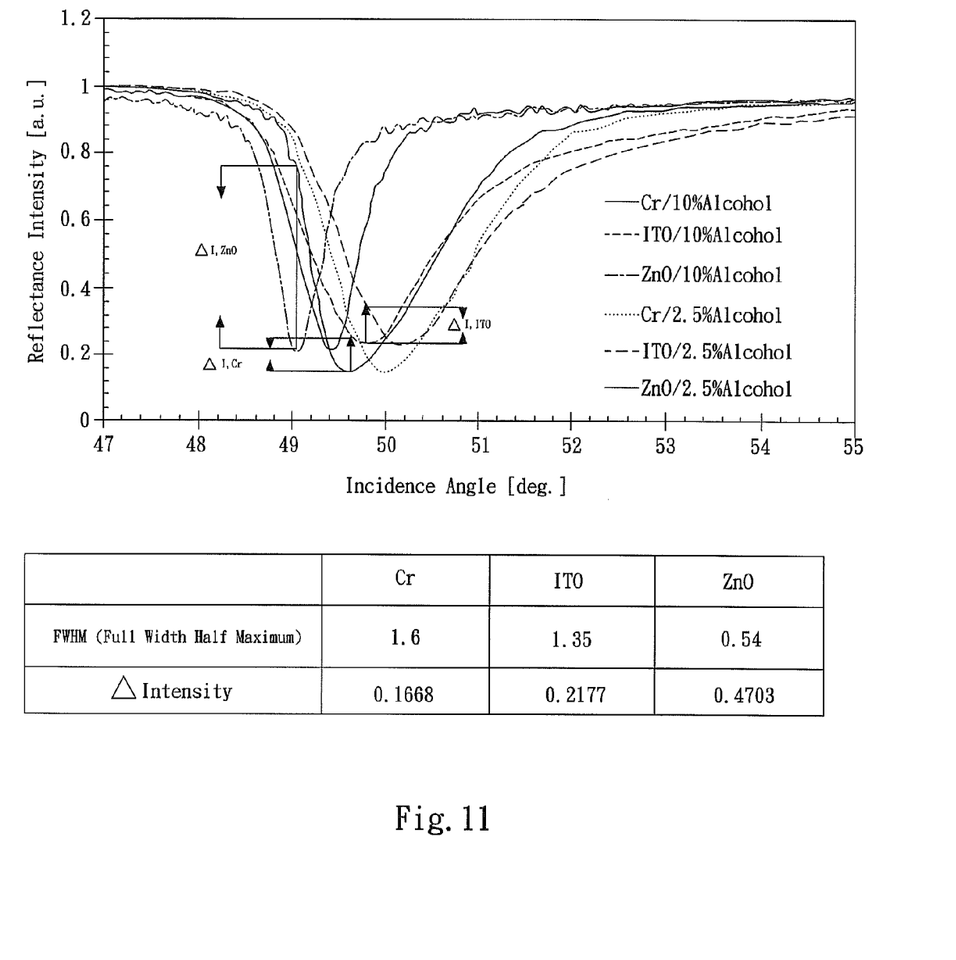
FIG. 11 shows a SPR characteristic curve of 2 nm, ITO 210 nm, ZnO 50 nm passing through an alcohol concentration of 2.5% and 10% respectively.
Figure 12:
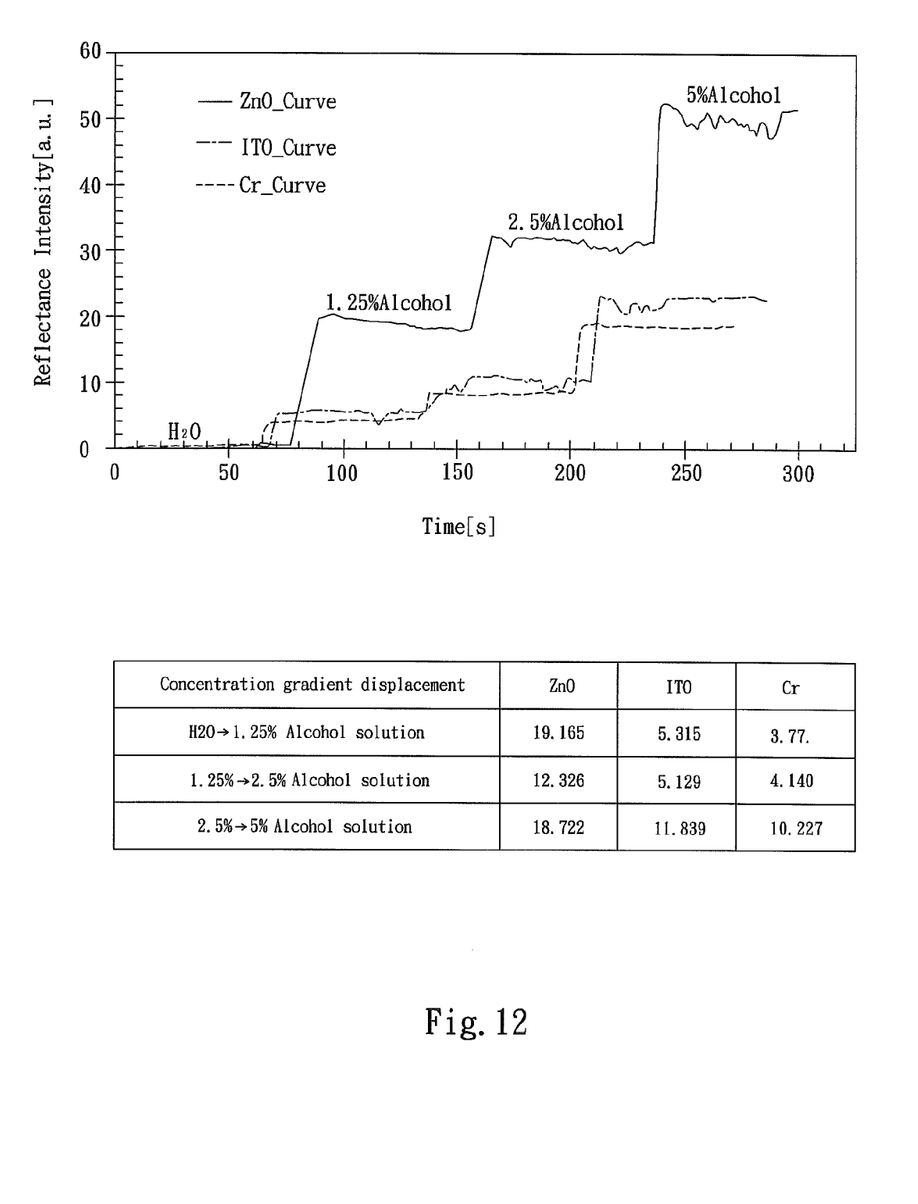
FIG. 12 shows a ladder diagram of the reflection intensities of a light passing into solutions of different refractive rates at a fixed angle.

It is noteworthy to point out that the zinc oxide film layer in the sensor chip is interfered by energies to produce a jump of energy level of electrons and release weak electromagnetic waves. The excited metal surface is synchronous with the strengthened surface plasmon resonance (SPR) mechanism, and thus the full width half maximum (FWHM) in the SPR becomes smaller and the effect on the property difference becomes larger as shown in FIGS. 11, 12 and Tables 1 and 2, which is the difference detected by a change of refractive index of an alcohol solution. With the aforementioned improvement, we can obtain a more sensitive and accurate sensing function, and the zinc oxide SPR sensor can be used for detecting a trace of tiny gas molecules and biomolecules.

TABLE 1

|  | Cr | ITO | ZnO |
|---|---|---|---|
| FWHM | 1.6 | 1.35 | 0.54 |
| ΔIntensity | 0.1668 | 0.2177 | 0.4703 |

TABLE 2

| Concentration gradient displacement | ZnO | ITO | Cr |
|---|---|---|---|
| H2O→1.25% Alcohol | 19.165 | 5.315 | 3.770 |
| 1.25%→2.5% Alcohol | 12.326 | 5.129 | 4.140 |
| 2.5%→5% Alcohol | 18.722 | 11.839 | 10.227 |

Intensity Attenuation Measuring Method

The intensity attenuation detection and analytical method adopt constant incident light wavelength (or resonant wavelength) and refractive index of a metal film to adjust the angle of the incident light until the SPR phenomenon occurs. In other words, the incident angle is adjusted to the SPR resonant angle, and such SPR resonant angle shows the refractive index caused by the dielectric layer of the chip. When comparing the original resonant angle of the chip, we can know that corresponding refractive index of the dielectric layer of the testing chip. To cope with the overall optical path structure, the external optical path is divided into signal optical path (passing through the SPR sensing chip) and a reference optical path (not passing through the SPR sensing chip), and the intensity or heterodyne interference measuring technique is used for eliminating noise signals such as stray lights or temperature variations from background signals. The devices of the embodiments are illustrated in details in FIGS. 7 to 10.

Resonant Wavelength Variation Detection and Analytical Method

The resonant wavelength variation detection and analytical method adopt constant transverse propagation length and use a white light source to adjust the angle of incident light according to the corresponding value of a known refractive index of a metal film that varies with wavelength, until the SPR occurs (or adjust the angle to the SPR resonant angle). A spectroscope is used to detect a reflected light, and the wavelength (which is the resonant wavelength) of absorbed incident light can be obtained from the spectrum, and thus the value of corresponding variation of the refractive index of the dielectric layer can be derived. To cope with the overall optical path structure, the external optical path is divided into signal optical path (passing through the SPR sensing chip) and a reference optical path (not passing through the SPR sensing chip), and background noises such as stray lights or temperature variations are eliminated. The devices of the embodiments are illustrated in details in FIGS. 7 to 10.

Referring to FIG. 11 for the data of resonant angles corresponding to the intensity of reflection produced by a SPR sensing chip of the prior art using chromium for the intermediate layer and a SPR sensing chip of the invention using zinc oxide (ZnO) and indium tin oxide (ITO) for the intermediate layer, the results are the same as those shown in FIG. 11. In FIG. 11, 2.5% and 10% ethanol is adopted as the testing solution, and the 2.5% and 10% ethanol solutions are measured by SPR sensing chips with a structure adopting chromium metal, zinc oxide and indium tin oxide as the intermediate layer as shown in FIG. 2, and the measured data of the intensity corresponding to the resonant angle is obtained.

In FIG. 11, the change of concentration of the testing solution will shift the maximum intensity absorbed by the SPR. For example, if the SPR sensing chip has an intermediate layer made of zinc oxide and the measuring object is a 2.5% ethanol solution, the maximum intensity absorbed by the SPR reaction occurs at an incident angle of 49.5 degrees; and if the measuring object is a 10% ethanol solution, then the maximum intensity absorbed by the SPR reaction occurs at an incident angle of 49 degree, and there is a difference of 0.5 degrees in angular displacement. Further, the level of a concentration change and the angular displacement show a correspondence relation, and thus a measurer can easily know about the concentration of testing matters included in the testing solution by measuring the maximum angular displacement of the absorbed light intensity due to a change of concentration. Even in a mixed solution, the wavelength of the incident light wavelength can be adjusted specifically to be identified by the spectrum, and we also can know about the concentration of a certain testing matter in a mixed solution easily.

In FIG. 11, we also can observe that if zinc oxide (ZnO) and indium tin oxide (ITO) is used for the intermediate layer, we can have the same detection sensitivity of the prior art that uses chromium for the intermediate layer as indicated in the SPR characteristic curve of zinc oxide, the indium tin oxide and the chromium metal for the intermediate layer and shown in FIG. 11. The curve of zinc oxide is obviously sharper than the curve of indium tin oxide and chromium metal, indicating that zinc oxide has a better measurement and reaction sensitivity. The full width half maximum (FWHM) and the intensity as shown in FIG. 11 are compared, and we know that the reaction sensitivity of zinc oxide is approximately twice as that of the indium tin oxide, and three times as that of the prior art chromium intermediate layer.

The same conclusion can be obtained from FIG. 12. FIG. 12 shows a graph of intensity versus time of three different intermediate layers recorded in the condition of measuring the concentration of 0, 1.25%, 2.5% and 5% alcohol solutions, and the measured constant angle is greater than the angle of maximum intensity of the absorbed light. From the concentration gradient displacement as shown in FIG. 12, we can observe that the reaction sensitivity of zinc oxide in an alcohol solution with a change of concentration from 0 to 2.5% is three times of the sensitivity of the indium tin oxide and chromium metal, and approximately twice of the sensitivity of indium tin oxide and chromium metal for a change of concentration of an alcohol solution from 2.5% to 5%, and thus providing an effect better than the material of the intermediate layer of the prior art.

While the invention has been described by means of specific embodiments, numerous modifications and variations could be made thereto by those skilled in the art without departing from the scope and spirit of the invention set forth in the claims.

What is claimed is:

1. An apparatus of detecting biochemical molecules and gases by using a surface plasmon resonance (SPR) molecular sensing technology, comprising:
   a coupler;
   a sensor chip;
   a cavity space, provided for a reaction of testing molecules;
   a detector; and
   an incident light source;
   wherein the sensor chip further comprises at least one layer of transparent substrate, at least one layer of conducting metal oxide intermediate layer and at least one layer of metal thin film layer.

2. The apparatus of claim 1, wherein the coupler is a prism, an optical grating device or a light guide device.

3. The apparatus of claim 2, wherein the coupler is made of BK7, SF10 or other material having a specific refractive index if the couple is a prism, and the angle of the coupler corresponds to the incident angle and can be a vertical incident angle or an oblique incident angle.

4. The apparatus of claim 1, wherein the transparent substrate is made of a material selected from the collection of glass, quartz, polymer and transparent high-dielectric thin film.

5. The apparatus of claim 1, wherein the transparent substrate, the conducting metal oxide intermediate layer and the metal thin film layer have a thickness ranging from 1 nm to 500 nm.

6. The apparatus of claim 1, wherein the substrate of the intermediate layer is made of zinc oxide, indium tin oxide, carbon nanotube, tin dioxide, titanium dioxide, tungsten oxide or any other transparent metal oxide with a good conductivity.

7. The apparatus of claim 1, wherein the incident light source is a visible light or a near infrared light having a wavelength from 400 nm to 1700 nm.

8. The apparatus of claim 1, wherein the structure of each layer of the sensor chip can be a structure formed by stacking one to twenty intermediate layers and metal layers with each other or a structure of interlacing the metal layers and the intermediate layers in any sequence, and further comprises a transparent substrate.

9. The apparatus of claim 1, wherein the metal layer is made of a material selected from the collection of gold, silver, copper, platinum, palladium, and any alloy and any coated structure of said materials.

10. The apparatus of claim 1, wherein the incident angle of the incident light source is from 30 degrees to 80 degrees.

11. The apparatus of claim 1, wherein the testing molecule is composed of a gas or liquid biomolecule and a chemical composition.

12. A detection method, using the apparatus of claim 1.

13. The method of claim 12, wherein the method can control a specific wavelength, a specific intensity or an incident angle as a variable.

14. The method of claim 12, wherein the method can perform a single point, one-dimensional or two-dimensional detection.

15. The method of claim 12, wherein the method can adopt an intensity detecting SPR measuring system or a phase detecting SRP measuring system.

* * * * *